(12) United States Patent
Chen

(10) Patent No.: US 9,949,774 B2
(45) Date of Patent: Apr. 24, 2018

(54) AXIAL COMPRESSION IMPLANT

(71) Applicant: Timothy Chen, Exton, PA (US)

(72) Inventor: Timothy Chen, Exton, PA (US)

( * ) Notice: Subject to any disclaimer, the term of this patent is extended or adjusted under 35 U.S.C. 154(b) by 0 days.

(21) Appl. No.: 15/165,708

(22) Filed: May 26, 2016

(65) Prior Publication Data

US 2017/0340370 A1 Nov. 30, 2017

(51) Int. Cl.
*A61B 17/86* (2006.01)
*A61F 2/42* (2006.01)

(52) U.S. Cl.
CPC ............ *A61B 17/86* (2013.01); *A61B 17/861* (2013.01); *A61B 17/863* (2013.01); *A61B 17/864* (2013.01)

(58) Field of Classification Search
CPC ...................................... A61B 17/86–17/8685
USPC ...................................................... 623/21.19
See application file for complete search history.

(56) References Cited

U.S. PATENT DOCUMENTS

| | | | | |
|---|---|---|---|---|
| 3,177,456 A * | 4/1965 | Haydu | ...................... | H01R 4/34 24/135 R |
| 4,640,271 A * | 2/1987 | Lower | ................ | A61B 17/8685 606/105 |
| 5,667,510 A | 9/1997 | Combs | | |
| 5,827,285 A * | 10/1998 | Bramlet | ................. | A61B 17/68 411/166 |
| 6,030,162 A * | 2/2000 | Huebner | ............ | A61B 17/1682 411/263 |
| 6,413,260 B1 * | 7/2002 | Berrevoets | ............. | A61B 17/68 606/304 |
| 6,458,134 B1 * | 10/2002 | Songer | ................... | A61B 17/68 606/304 |
| 6,517,543 B1 * | 2/2003 | Berrevoets | ............. | A61B 17/68 411/324 |
| 7,951,198 B2 * | 5/2011 | Sucec | .................. | A61B 17/562 606/300 |
| 8,529,611 B2 | 9/2013 | Champagne et al. | | |
| 8,834,572 B2 | 9/2014 | Averous et al. | | |
| 8,998,999 B2 | 4/2015 | Lewis et al. | | |
| 9,011,504 B2 | 4/2015 | Reed | | |
| 9,044,287 B2 | 6/2015 | Reed et al. | | |

(Continued)

FOREIGN PATENT DOCUMENTS

CN 201420183071 4/2014
WO WO2015147846 10/2015

(Continued)

OTHER PUBLICATIONS

Nextremity Solutions one-sheet. Undated. One page.
Arthrex RetroFusion Screw brochure. 2016. 4 pages.
PHALINX Hammertoe Fixation System. 2016. 2 pages.

*Primary Examiner* — Zade Coley
(74) *Attorney, Agent, or Firm* — Joseph E. Maenner; Maenner & Associates, LLC

(57) ABSTRACT

In described embodiments, an implant assembly includes a first implant having a body with a first end and a second end and a hollow passage extending therethrough between the first end and the second end. The first implant is sized for insertion into a first bone segment. A connector has a first end rotatably connected to the first implant at the first end of the first implant, a second end insertable into a second bone segment, and a connector body extending through the hollow passage of the first connector. A method of inserting the implant assembly is also provided.

18 Claims, 19 Drawing Sheets

(56) References Cited

U.S. PATENT DOCUMENTS

| | | | |
|---|---|---|---|
| 9,072,561 B2 * | 7/2015 | Jacofsky | A61B 17/686 |
| 9,138,274 B1 | 9/2015 | Biesinger et al. | |
| D749,738 S | 2/2016 | Weiner et al. | |
| 9,271,775 B2 | 3/2016 | Lavi | |
| 2001/0000186 A1 | 4/2001 | Bramlet et al. | |
| 2006/0056933 A1 * | 3/2006 | Guy | B23B 31/006 |
| | | | 409/234 |
| 2010/0023057 A1 | 1/2010 | Aeschlimann et al. | |
| 2011/0004255 A1 | 1/2011 | Weiner et al. | |
| 2011/0054545 A1 * | 3/2011 | Champagne | A61B 17/7225 |
| | | | 606/301 |
| 2011/0301652 A1 | 12/2011 | Reed et al. | |
| 2012/0065692 A1 | 3/2012 | Champagne et al. | |
| 2013/0165982 A1 | 6/2013 | Ek et al. | |
| 2013/0184708 A1 | 7/2013 | Robinson et al. | |
| 2013/0325138 A1 | 12/2013 | Graham | |
| 2014/0107712 A1 | 4/2014 | Fallin et al. | |
| 2014/0214080 A1 | 7/2014 | Wales et al. | |
| 2014/0343616 A1 | 11/2014 | Sellers | |
| 2015/0012050 A1 | 1/2015 | Anderson | |
| 2015/0088136 A1 | 3/2015 | Kotyljac et al. | |
| 2015/0094778 A1 | 4/2015 | McCormick et al. | |
| 2015/0223850 A1 | 8/2015 | Reed | |

FOREIGN PATENT DOCUMENTS

| | | |
|---|---|---|
| WO | WO2015147847 | 10/2015 |
| WO | WO2016044053 | 3/2016 |

\* cited by examiner

AXIAL COMPRESSION IMPLANT

BACKGROUND OF THE INVENTION

Field of the Invention

The present invention relates to medical implants, and, in particular, to implants for the treatment of digital deformities, such as hammer toe.

Description of the Related Art

A digital deformity, such as hammer toe, is a deformity of the second, third or fourth digit. In this condition, the digit is bent at the middle joint, so that the digit resembles a hammer. Initially, digital deformities can be flexible and can be corrected with simple measures but if left untreated, they can become fixed and require surgery.

It would be beneficial to provide a surgical implant that can correct a digital deformity and provide small joint fusion.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention provides an implant assembly including a first implant having a body with a first end and a second end and a hollow passage extending therethrough between the first end and the second end. The first implant is sized for insertion into a first bone segment. A connector has a first end rotatably connected to the first implant at the first end of the first implant, a second end insertable into a second bone segment, and a connector body extending through the hollow passage of the first connector.

In an alternative embodiment, the present invention also provides a method for inserting the implant assembly described above.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 7I shows the guide wire having been inserted through the passage to extend distally of the third bone segment and the first implant;

DETAILED DESCRIPTION

Figure 1:
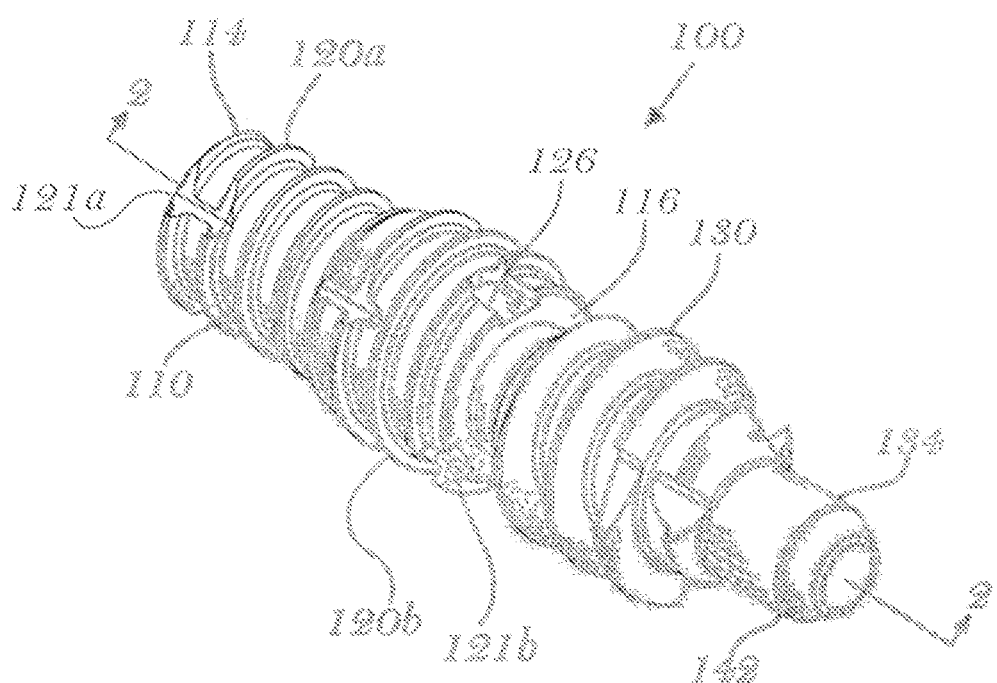
FIG. 1 is a perspective view of a compression implant assembly according to a first exemplary embodiment of the present invention.

In the drawings, like numerals indicate like elements throughout. Certain terminology is used herein for convenience only and is not to be taken as a limitation on the present invention. The terminology includes the words specifically mentioned, derivatives thereof and words of similar import. As used herein, the term "proximal" is intended to mean a direction closer to the ankle of the patient in whom the inventive implant is being inserted, and "distal" is intended to mean a direction closer to the tip of the toe of the patient in whom the inventive implant is being inserted.

The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Referring to the figures, a surgical implant assembly for the treatment of a digital deformity is disclosed. While the deformity discussed in detail below is hammer toe, those skilled in the art will recognize that the deformity addressed by the present invention can address other deformities as well. For example, the present invention can be used to secure two adjacent bones or bone fragments to each other, such as in repairing a bone break. For purposes of the detailed description below, however, the present invention will be described as being used in the treatment/correction of a hammer toe condition.

Figure 2:
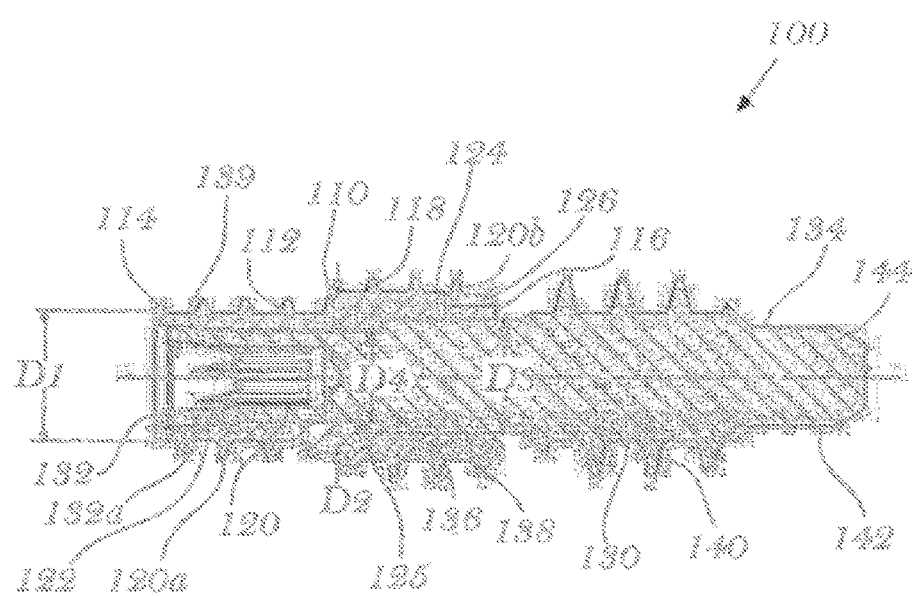
FIG. 2 is a sectional view of the implant assembly shown in FIG. 1.
Figure 3:
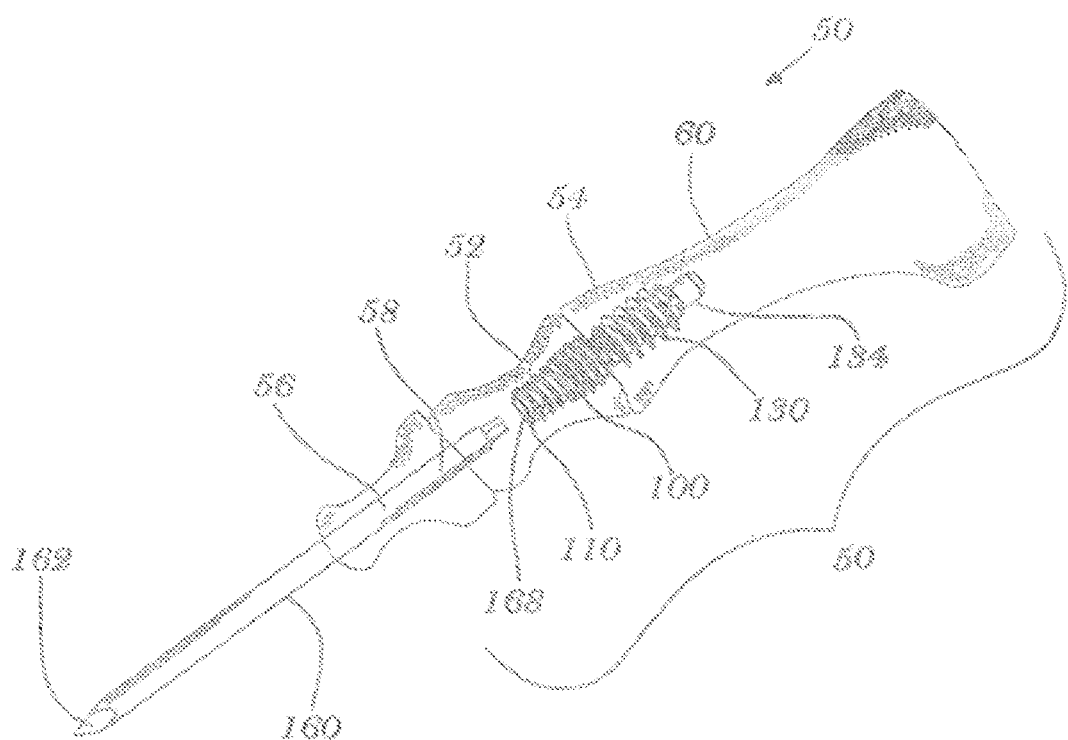
FIG. 3 is a perspective view of the implant assembly shown in FIG. 1, inserted into adjacent bone segments, and a guide wire used to facilitate insertion of the implant assembly.

A first exemplary embodiment of an implant assembly 100 ("assembly 100") is shown in FIGS. 1-3. Assembly 100 includes a distal, or first, implant 110 and a connector 130 that is rotatably connected to and extends outwardly from first implant 110 such that first implant 110 is fixedly inserted into a first bone portion and connector 130 extends into a second, adjacent bone portion to secure second bone portion to first bone portion.

Implant 110 has a body 112 with a first end 114 and a second end 116. A hollow passage 118 extends through body 112 between first end 114 and second end 116. First implant 110 is sized for insertion into a first bone segment, such as, for example, a middle phalanx 52 in a toe 50.

First implant 110 has an external thread 120 extending outwardly from body 112. External thread 120 includes a thread 120a at first end 114 having a first thread pitch and a thread 120b at second end 116 having a second thread pitch. The second pitch is different from the first pitch to better match the bone anatomy. Optionally, as shown in FIG. 1, thread 120a can include a cut portion 121a that provides a self-tapping feature. Similarly, thread 120b includes a cut portion 121b, also for providing a self-tapping feature. Thread 120 is adapted to retain first implant 110 in first bone segment 52.

Body 112 has a first outer diameter D1 proximate to first end 114 and a second outer diameter D2, larger than first outer diameter D1, proximate to second end 116. D2 is larger than D1 in cases where the diameter of the bone into which first implant 110 is being inserted is wider at second end 116 than at first end 114, particularly with respect to middle phalanx 52.

Hollow passage 118 comprises a tapered portion 122 proximate to first end 114. A first portion 124 of hollow passage 118 has a first diameter D3 proximate to second end 116. A second portion 125 of hollow passage 118 extends between tapered portion 122 and first portion 124 and has a second diameter D4, smaller than first diameter D3. A lip 127 marks the change between first diameter D3 and second diameter D4.

Second end 116 of first implant 110 includes a driver receptacle 126. In an exemplary embodiment, driver receptacle 126 is externally cut in thread 120b, although those skilled in the art will recognize that driver receptacle 126 can be cut into second end 116. Driver receptacle 126 accepts a spanner (not shown) that engages first implant 110 and is used to threadingly advance first implant 110 into middle phalanx 52.

Connector 130 has a first end 132 rotatably mounted in and connected to first implant 110 at first end 114 of first implant 110 and a second end 134 extending outwardly from second end 116 of body 112. Second end 134 is insertable into a second bone segment, such as, for example, a proximal phalanx 54 as shown in FIG. 3. A connector body 136 extends through hollow passage 118 of first connector 110.

Connector body 136 has a first body portion 138 located in first portion 124 of the hollow passage 118 such that first body portion 138 has a larger outer diameter than second diameter D4 of second portion 125. Connector 130 is inserted into passage 118 from second end 116 until first body portion 138 engages lip 127. Connector first end 132 is then swaged to expand the diameter of first end 132 within tapered portion 122 so that connector 130 cannot be removed from passage 118.

Connector first end 132 includes a driver receptacle 139 that is used to rotate connector 130 with respect to first implant 110. Driver receptacle 139 can be a hex opening sized to accept an Allen wrench, a star shaped opening sized to accept a Torx® wrench, or other suitable sized and shaped opening or connection.

Connector second end 134 has an externally threaded portion 140 that is adapted to retain connector 130 in second bone segment 54, adjacent first bone segment 52. Externally threaded portion 140 includes a thread pitch that is the same as the thread pitch of thread 120b at second end 116 of first implant 110.

Optionally, connector second end 134 also includes an unthreaded portion 142 adjacent to threaded portion 140 and distal from connector first end 132. Unthreaded portion 142 can be used as a guide to guide connector 130 into a passage formed in second bone segment 54, as will be discussed later herein. Unthreaded portion 142 can include a chamfer 144 that assists in leading connector 130 into a passage formed in second bone segment 54.

An exemplary method of inserting assembly 100 into toe 50 will now be described. It is noted that the steps described below are not necessarily need to be performed in the order described. Referring now to FIG. 3, a guide wire 160 is used to assist in the insertion of implant 110 into first bone segment 52.

A passage 58 is drilled distally through first bone segment 52, as well as through third bone segment (distal phalanx) 56 and out the distal tip of toe 50. Guide wire 160 is inserted through passage 58 such that distal tip 162 extends distally of toe 50.

The proximal end of passage 58 is widened sufficiently to allow for the threaded insertion of implant 110 into passage 58 by inserting a spanner wrench into driver receptacle 126 and using the spanner wrench to rotate implant 110, threading implant 110 into passage 58 such that proximal end 116 of implant 110 is flush with the proximal end of first bone segment 52.

A passage 60 is then drilled proximally from the distal end of second bone segment 54 sufficiently long enough to allow for the insertion of second end 134 of connector 130.

Guide wire 160 is translated proximally, such that a proximal tip 168 is inserted into driver receptacle 139 of connector 130 such that rotation of guide wire 160 also rotates connector 130. Second end 134 of connector 130 is inserted into passage 60 in second bone segment 54. Chamfer 144 on unthreaded portion 142 provides a lead into passage 60 and, once unthreaded portion 142 is in passage 60, guide wire 160 is rotated such that thread 140 digs into the bone surrounding passage 60, securing connector 130 to second bone segment 54 and drawing second bone segment 54 against first bone segment 52.

Figure 4:
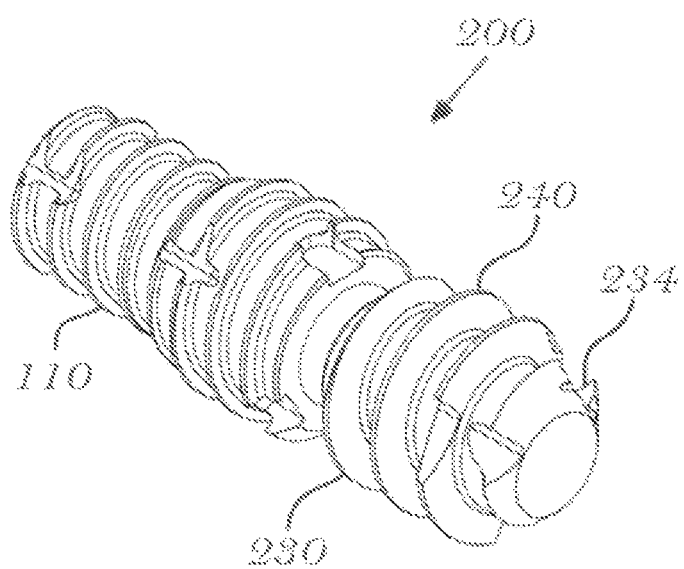
FIG. 4 is a perspective view of a compression implant assembly according to a second exemplary embodiment of the present invention.
Figure 5:
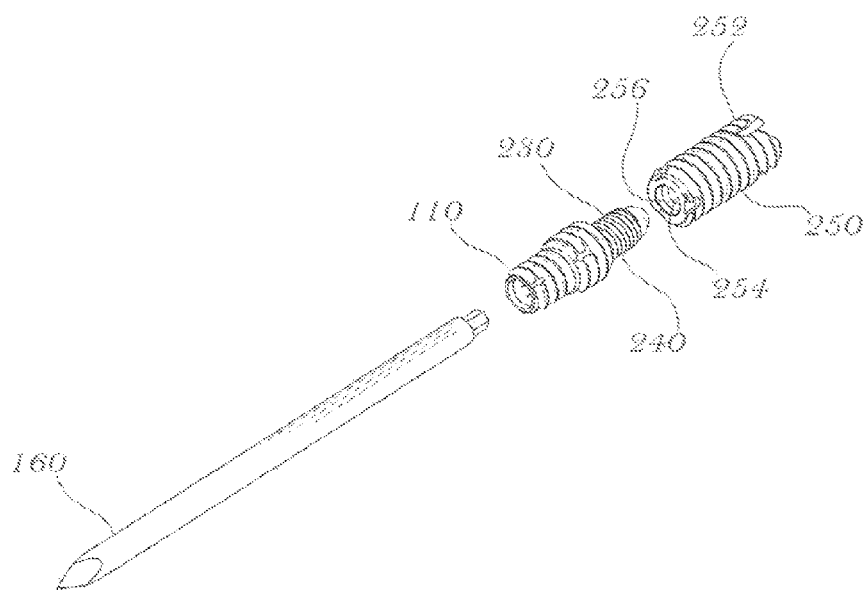
FIG. 5 is a perspective view of the implant assembly shown in FIG. 4, with an associated guide wire.
Figure 6:
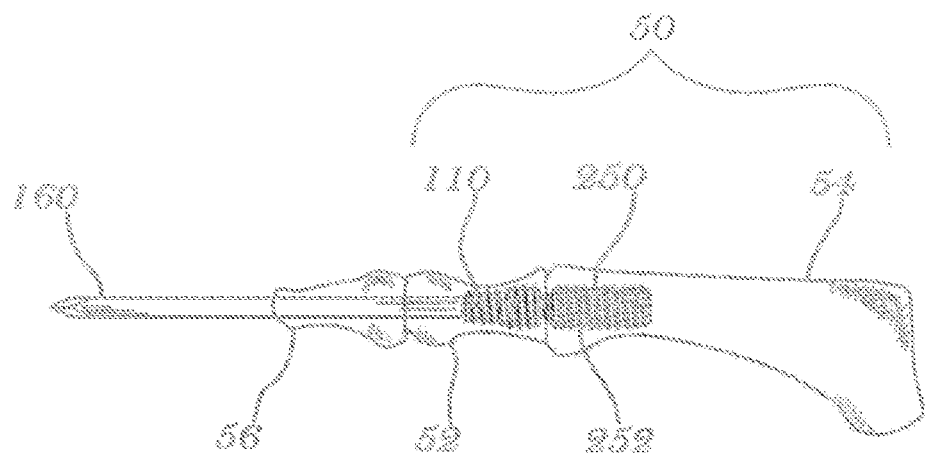
FIG. 6 is a side elevational view of the implant assembly with guide wire shown in FIG. 6 inserted into adjacent bone segments.

In an alternative embodiment of an implant assembly 200 ("assembly 200"), shown in FIGS. 4-6, first implant 110 is used with a connector 230. Connector 230 is generally identical to connector 130, with the exception that unthreaded portion 142 is omitted. Implant assembly 200 includes a proximal, or second, implant 250 that is sized for insertion into second bone segment 54. Second implant 250 further comprises an external thread 252 that adapted to retain second implant 250 in second bone segment 54.

Implant 250 also includes an internal passage 254 that sized to accept connector 230. An internal thread 256 inside passage 252 is adapted to threadingly engage threaded portion 240 on connector second end 234.

Figure 7A:
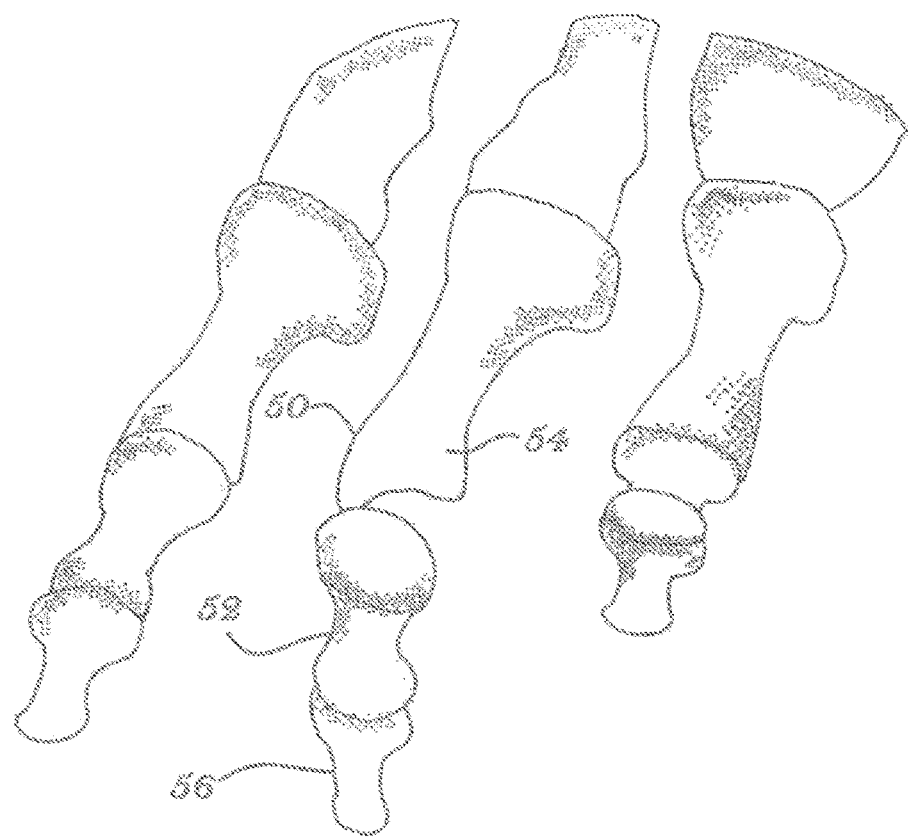
FIG. 7A shows a first bone segment distended from a second bone segment.
Figure 7B:
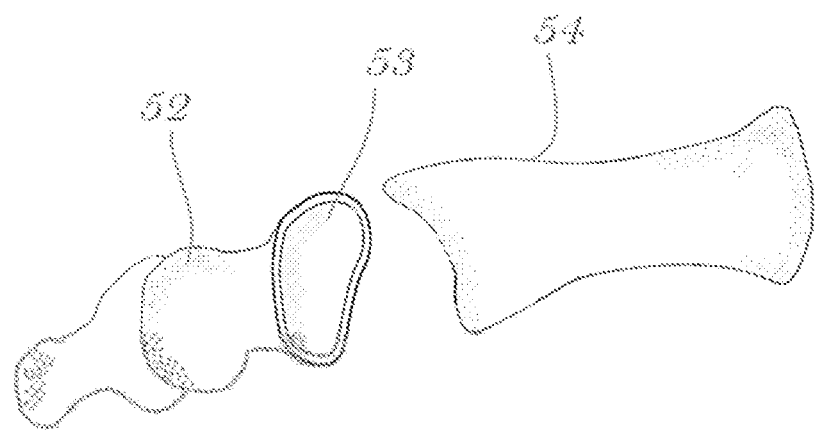
FIG. 7B show an osteotomy having been performed on the first bone segment at the second bone segment, forming a planar surface.
Figure 7C:
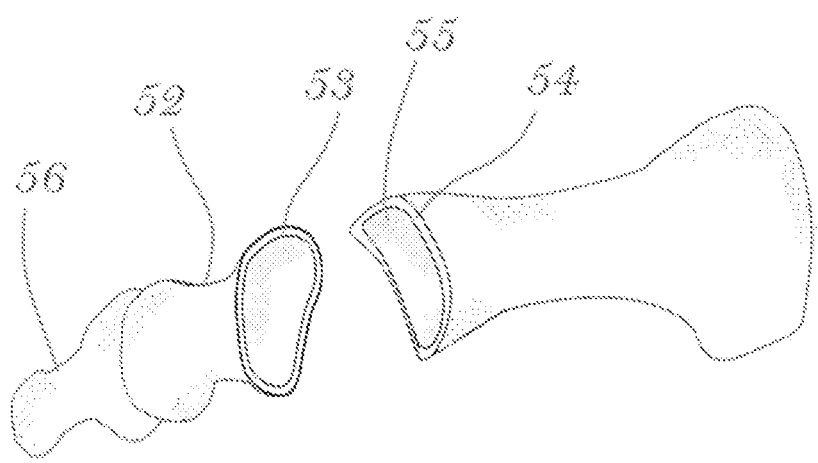
FIG. 7C shows an osteotomy having been performed on the second bone segment at the first bone segmen, forming a planar surface.

Referring to FIGS. 7A-7J, assembly 200 can be inserted into toe 50 as follows. As shown in FIG. 7A, first bone segment 52 is distended from second bone segment 54. As shown in FIG. 7B, an osteotomy is performed on first bone segment 52 at second bone segment 54, forming a planar surface 53. Similarly, as shown in FIG. 7C, an osteotomy is performed on second bone segment 54 at first bone segment 52, forming a planar surface 55.

Figure 7D:
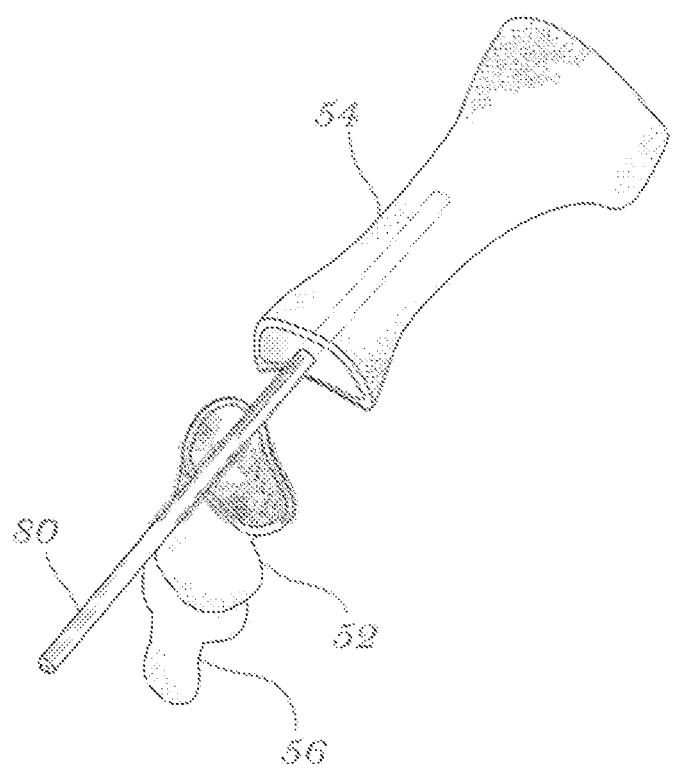
FIG. 7D shows a guide wire 80 being inserted into the second bone segment.
Figure 7E:
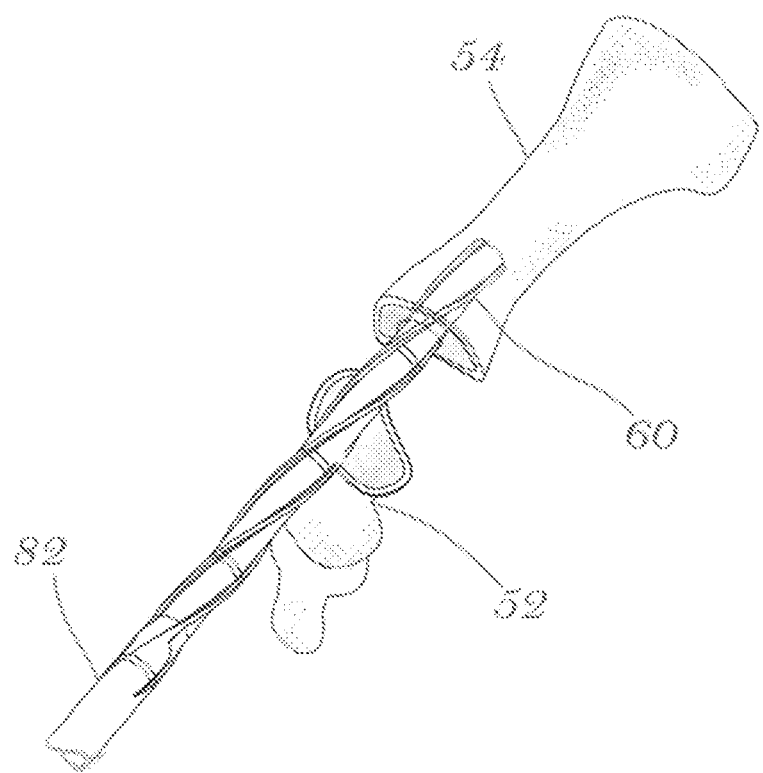
FIG. 7E shows a drill being inserted into the guide wire passage.
Figure 7F:
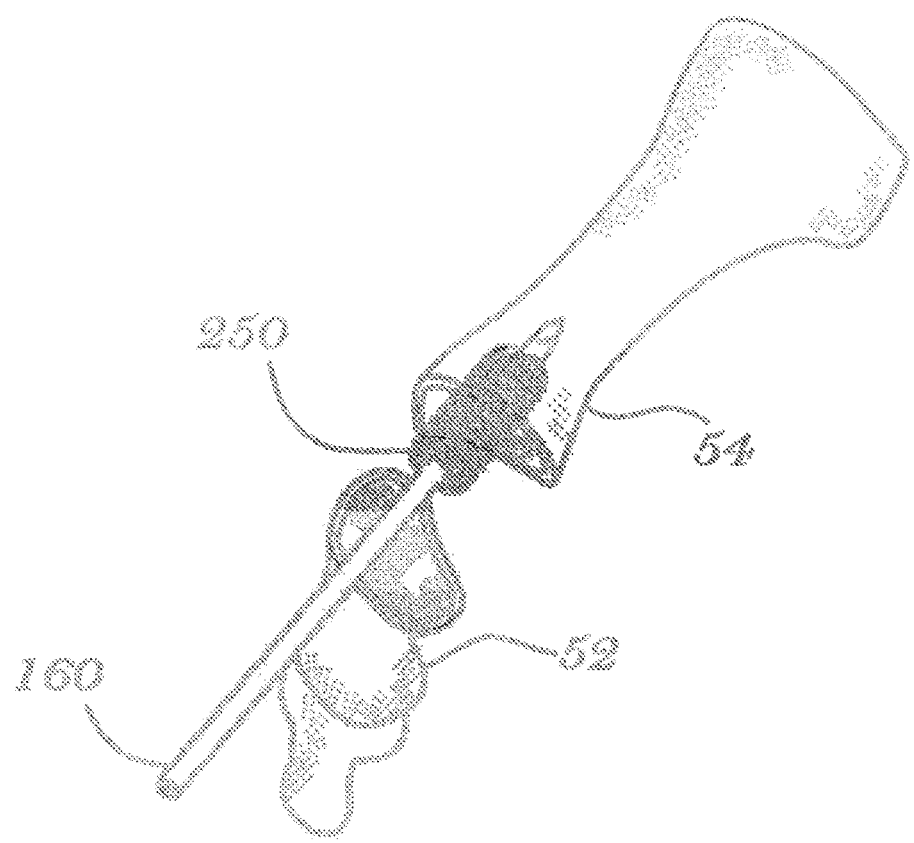
FIG. 7F shows a second implant inserted into the passage 60 using the guide wire.
Figure 7G:
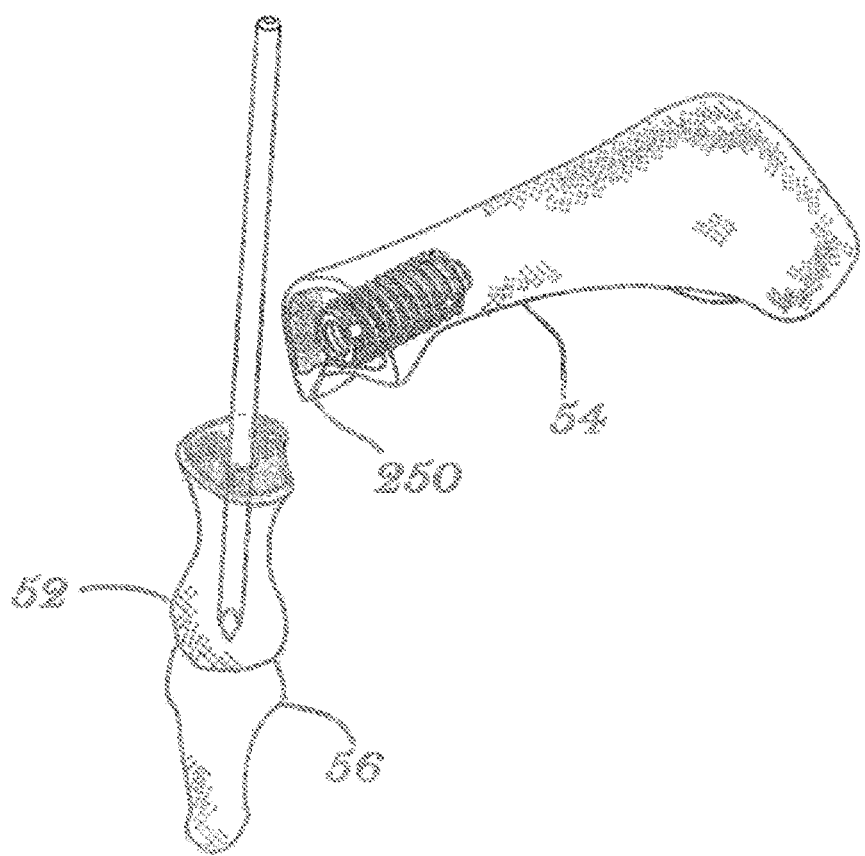
FIG. 7G shows the guide wire being inserted through the first bone segment and the third bone segment, forming a pilot hole.
Figure 7H:
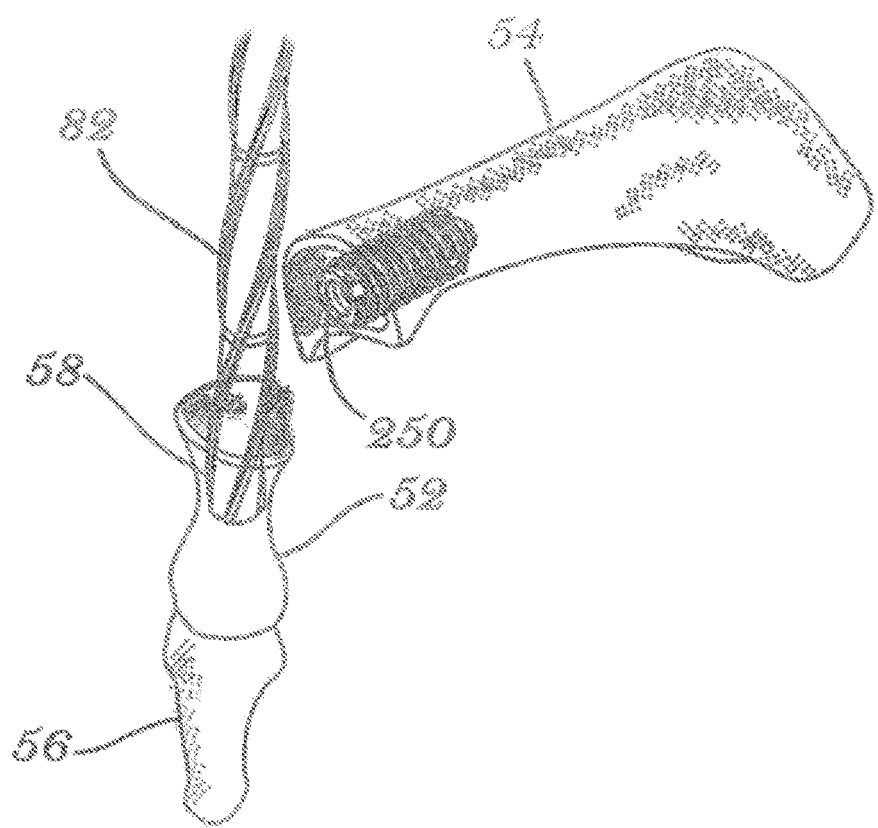
FIG. 7H shows the drill inserted into the pilot hole, forming a passage.
Figure 71:
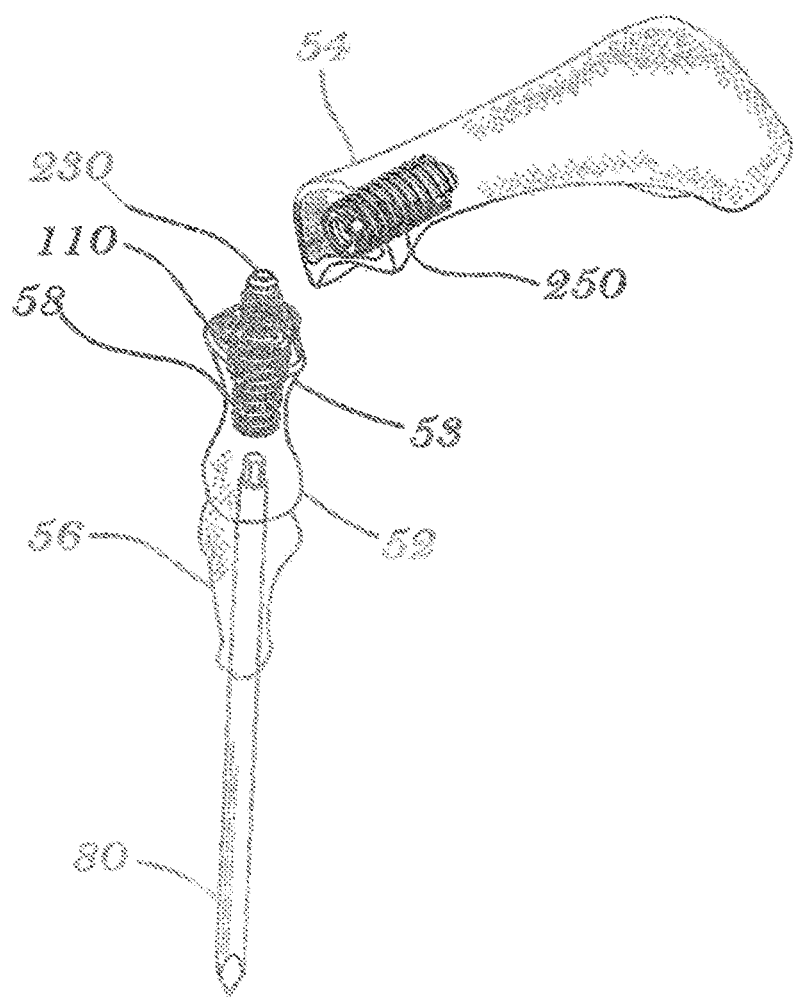
Figure 7J:
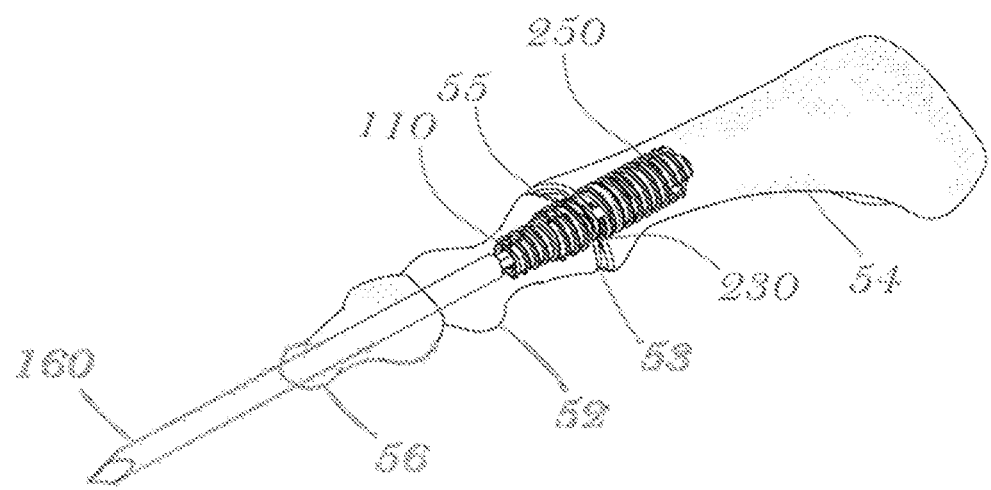
FIG. 7J shows the planar surfaces aligned and butted up against each other so that the guide wire can rotate the connector for threaded connection with the second implant.

FIG. 7D shows a guide wire 80 being inserted into second bone segment 54 to provide a pilot hole for a drill 82, shown in FIG. 7E, which forms passage 60 in second bone segment 54. Second implant 250 is inserted into passage 60 using guide wire 160, as shown in FIG. 7F. FIG. 7G shows guide wire 80 being inserted through first bone segment 52 and third bone segment 56 forming a pilot hole, while FIG. 7H shows drill 82 inserted into the pilot hole, forming passage 58. FIG. 7I shows guide wire having been inserted through passage 58 to extend distally of third bone segment 56 and first implant 110 with connector 230 also inserted into passage 58 from planar surface 53. FIG. 7J shows planar surfaces 53, 55 aligned and butted up against each other so that guide wire 160 can rotate connector 230 for threaded connection with second implant 250, securing first bone segment 52 against second bone segment 54.

Figure 8:
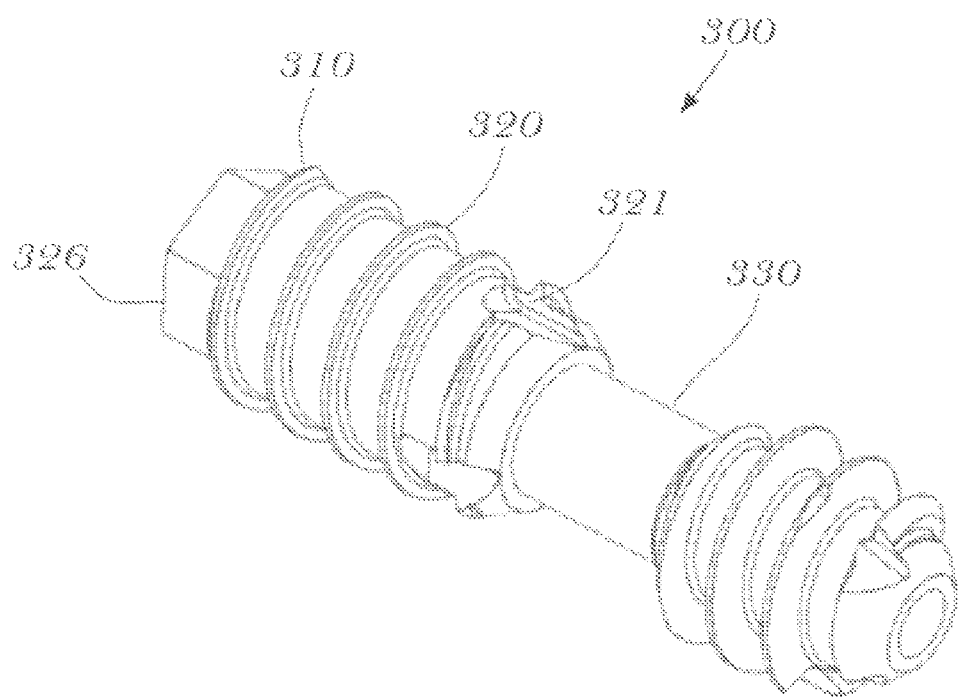
FIG. 8 is a perspective view of a compression implant assembly according to a third exemplary embodiment of the present invention.
Figure 9:
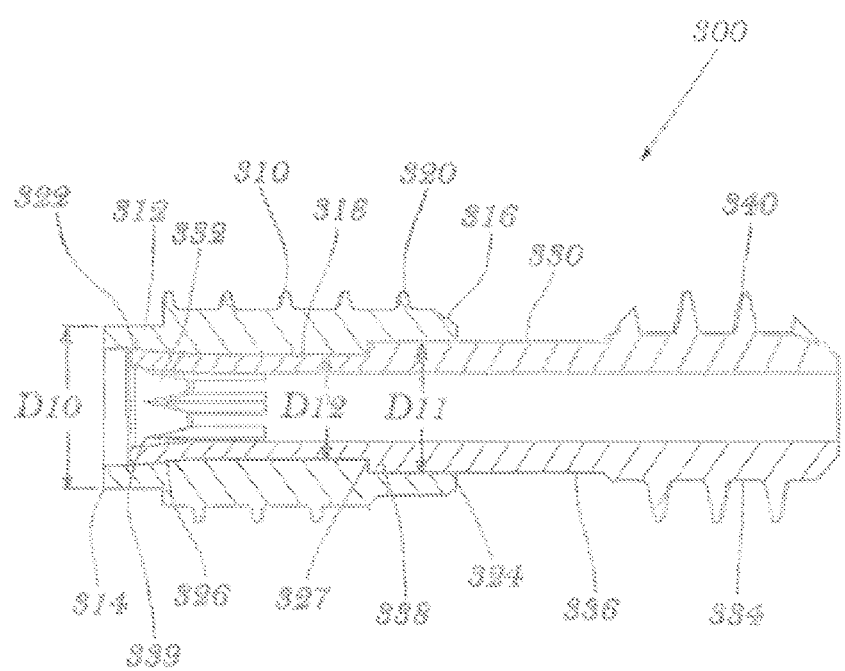
FIG. 9 is a sectional view of the assembly of FIG. 8.
Figure 10:
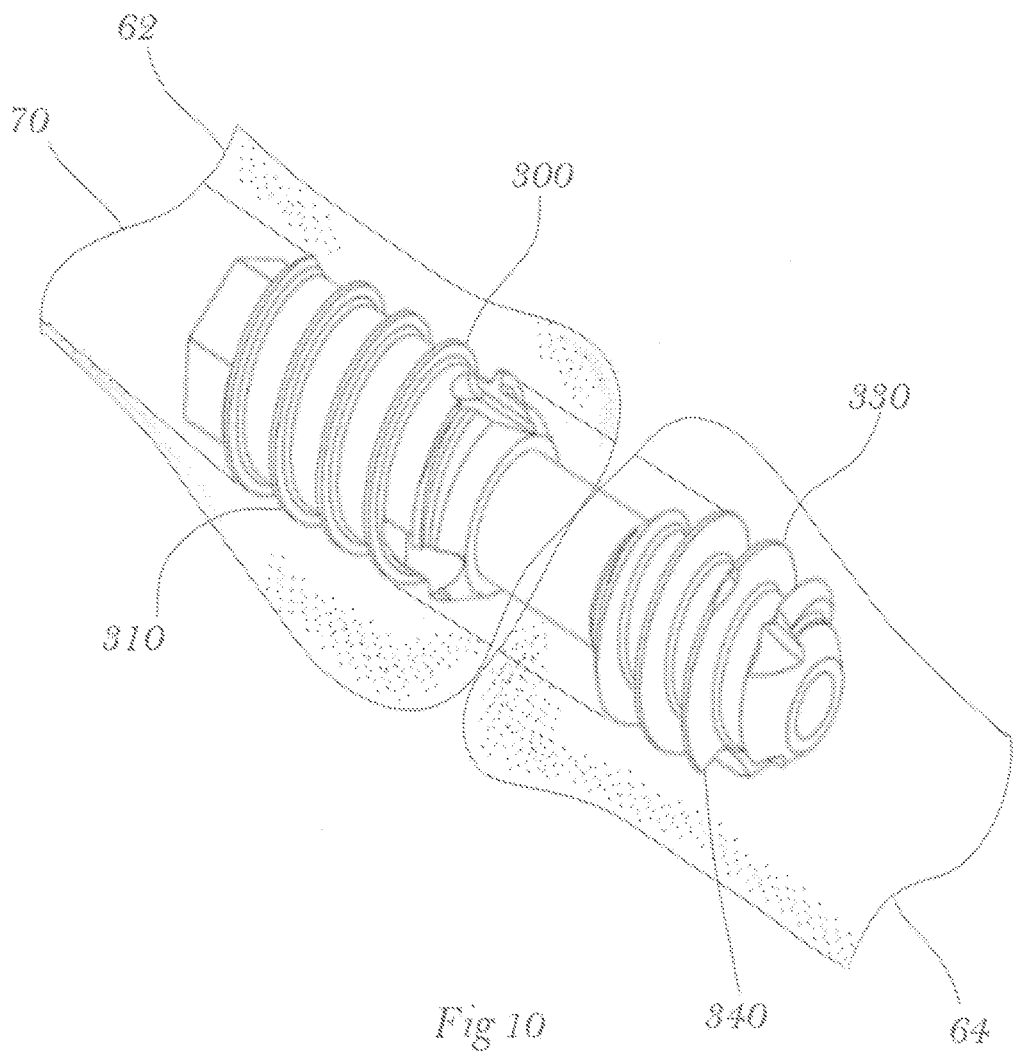
FIG. 10 is a side elevational view of the implant assembly shown in FIG. 9 inserted into adjacent bone segments.

In another alternative embodiment of an implant assembly 300 ("assembly 300"), shown in FIGS. 8-10, assembly 300 can be used as a compression screw, such as to connect two pieces of broken bone to each other. Assembly 300 includes a distal, or first, implant 310 and a connector 330 that is rotatably connected to and extends outwardly from first implant 310 such that first implant 310 is fixedly inserted into a first bone portion and connector 330 extends into a second, adjacent bone portion to secure second bone portion to first bone portion.

Implant 310 has a body 312 with a first end 314 and a second end 316. A hollow passage 318 extends through body 312 between first end 314 and second end 316. Implant 310 is sized for insertion into a first bone portion 62, of a broken bone 60.

Implant 310 has an external thread 320 extending outwardly from body 312. Optionally, as shown in FIG. 8, thread 320 can include a cut portion 321. Thread 320 has a first thread pitch.

Body 312 has a first outer diameter D10. Hollow passage 318 comprises a tapered portion 322 proximate to first end 314. A first portion 324 of hollow passage 318 has a first diameter D11 proximate to second end 316. A second portion 326 of hollow passage 318 extends between tapered portion 322 and first portion 324 and has a second diameter D12, smaller than first diameter D11. A lip 327 marks the change between first diameter D11 and second diameter D12.

First end 316 of first implant 310 includes a driver receptacle 326. In an exemplary embodiment, driver receptacle 326 is a hex head that can be engaged by a socket wrench (not shown) or other similar driver, although those skilled in the art will recognize that driver receptacle 326 can be other shapes. Driver receptacle 326 is used to threadingly advance first implant 310 into first bone portion 62 toward second bone portion 64.

Connector 330 has a first end 332 rotatably mounted in and connected to implant 310 at first end 314 of implant 310 and a second end 334 extending outwardly from second end 316 of body 312. Second end 334 is insertable into a second bone segment 64, as shown in FIG. 10. A connector body 336 extends through hollow passage 318 of implant 310.

Connector body 336 has a first body portion 338 located in first portion 324 of the hollow passage 318 such that first body portion 338 has a larger outer diameter than second diameter D12 of second portion 326. Connector 330 is inserted into passage 318 from second end 316 until first body portion 338 engages lip 327. Connector first end 332 is then swaged to expand the diameter of first end 332 within tapered portion 322 so that connector 330 cannot be removed from passage 318.

Connector first end 332 includes a driver receptacle 339 that is used to rotate connector 330 with respect to implant 310. Driver receptacle 339 can be a hex opening sized to accept an Allen wrench, a star shaped opening sized to accept a Torx® wrench, or other suitable sized and shaped opening or connection.

Connector second end 334 has an externally threaded portion 340 that is adapted to retain connector 330 in second bone segment 64, adjacent first bone segment 62. Externally threaded portion 340 includes a thread pitch that is coarser than the thread pitch of thread 120 of implant 310.

To insert implant 300 into bone segments 62, 64, bone segments 62, 64 can be aligned, such as by using X-ray. A pilot hole 70 can be drilled obliquely relative to the length of each of bone segments 62, 64 and long enough to extend through bone segment 62 and into bone segment 64.

A driver (not shown) is attached to both driver receptacle 326 and driver receptacle 339. Connector second end 334 is inserted into pilot hole 70. Connector 330 is threaded into and through first bone segment 62 until thread 320 engages first bone segment 62, at which time, both threads 320, 340 thread through bone segment until connector 330 threads into second bone segment 64.

When implant 310 is fully inserted into first bone segment 62 and connector body 336 straddles both first bone segment 62 and second bone segment 64, as shown in FIG. 10, only driver receptacle 339 is rotated to advance connector 330 into second bone segment 64, drawing second bone segment 64 toward first bone segment 62, securing bone segments 62, 64 together.

It will be further understood that various changes in the details, materials, and arrangements of the parts which have been described and illustrated in order to explain the nature of this invention may be made by those skilled in the art without departing from the scope of the invention as expressed in the following claims.

I claim:

1. An implant assembly comprising:
    (a) a first implant having a body with a first end and a second end and a hollow passage extending therethrough between the first end and the second end, the first implant sized for insertion into a first bone segment;
    (b) a single-piece connector having a first end rotatably engaging the first implant at the first end of the first implant, a connector body extending through the hollow passage of the first implant from the first end of the first implant to the second end of the first implant, and a second end attached to the connector body and extending outwardly from the first implant, wherein the second end of the connector includes an external thread; and
    (c) a second implant sized for insertion into the second bone segment and having an internal thread sized to receive and retain the external thread on the connector.

2. The implant assembly according to claim 1, wherein the second end of the connector includes an unthreaded end adjacent to the external thread, distal from the first end of the connector.

3. The implant assembly according to claim 1, wherein the external thread is adapted to retain the connector in the second bone segment.

4. The implant assembly according to claim 1, wherein the second implant further comprises an external thread adapted to retain the second implant in the second bone segment.

5. The implant assembly according to claim 1, wherein the first implant has an external thread adapted to retain the first implant in the first bone segment.

6. The implant assembly according to claim 1, wherein the first end of the connector is disposed in the hollow passage.

7. The implant assembly according to claim 1, wherein the first end of the connector includes a driver receptacle.

8. The implant assembly according to claim 7, wherein the driver receptacle is outwardly flared.

9. The implant assembly according to claim 1, wherein the second end of the first implant includes a driver receptacle.

10. The implant assembly according to claim 1, wherein the body of the first implant has a first outer diameter proximate to the first end and a second outer diameter, larger than the first outer diameter, proximate to the second end.

11. The implant assembly according to claim 1, wherein the hollow passage comprises a tapered portion proximate to the first end, a first portion having a first diameter proximate to the second end, and a second portion between the tapered portion and the first portion, the second portion having a second diameter, smaller than the first diameter.

12. The implant assembly according to claim 11, wherein the connector body has a first body portion in the first portion of the hollow passage, the first body portion having a larger outer diameter than the second diameter of the second portion.

13. An implant assembly comprising:
    a distal implant having a hollow body, the hollow body having a first end having a first exterior thread and a second end having a second exterior thread, different from the first thread and a lip inside the hollow body between the first end and the second end, the lip defining a change from a first inner diameter of the hollow body at the first end of the body to a second inner diameter, larger than the first inner diameter, at the second end of the body; and
    a connector having a connector swaged first end rotatably mounted in the hollow body at the first end of the distal implant and a connector second end extending outwardly from the second end of the hollow body and exteriorly from the distal implant the connector having a first connector diameter sized to fit into the first inner diameter and a second connector diameter, larger than the first connector diameter, sized to fit into the second inner diameter.

14. The implant assembly according to claim 13, wherein the connector second end has a threaded portion and an unthreaded portion adjacent to the threaded portion, distal from the connector first end.

15. The implant assembly according to claim 14, further comprising a proximal implant comprising an internal thread adapted to threadingly engage the threaded portion on the connector second end.

16. The implant assembly according to claim 13, wherein the first end of the distal implant has a first diameter and wherein the second end of the distal implant has a second diameter, larger than the first diameter.

17. The implant assembly according to claim 13, wherein the distal implant is adapted to be inserted into a first bone portion and wherein the connector second end is adapted to be inserted into a second bone portion, adjacent to the first bone portion.

18. The implant assembly according to claim 13, wherein the connector first end includes a driver receptacle.

* * * * *